United States Patent [19]
Chan et al.

[11] Patent Number: 5,744,971
[45] Date of Patent: Apr. 28, 1998

[54] DEVICE AND APPARATUS FOR MEASURING DIELECTRIC PROPERTIES OF MATERIALS

[76] Inventors: Tsing Yee Amy Chan; Marianne Odlyha, both of Birkbeck College, University of London, 29 Gordon Square, London, Great Britain, WC1H 0PP

[21] Appl. No.: 524,759

[22] Filed: Sep. 7, 1995

[30] Foreign Application Priority Data

Sep. 9, 1994 [GB] United Kingdom ............... 9418183

[51] Int. Cl.[6] .................................................. G01N 22/04
[52] U.S. Cl. ............................................. 324/643; 324/642
[58] Field of Search ............................ 324/637, 639, 324/640, 642, 643, 644, 646, 638; 343/791

[56] References Cited

U.S. PATENT DOCUMENTS

| | | | |
|---|---|---|---|
| 4,544,880 | 10/1985 | Nagy | 324/642 |
| 5,059,914 | 10/1991 | Lacombe | 324/602 |
| 5,227,730 | 7/1993 | King et al. | 324/642 X |
| 5,233,306 | 8/1993 | Misra | 324/601 |

FOREIGN PATENT DOCUMENTS

| | | |
|---|---|---|
| 2 166 249 | 4/1986 | United Kingdom . |
| 2194340 | 3/1988 | United Kingdom ............... 324/643 |

OTHER PUBLICATIONS

Athey et al. "Measurements of Radio Frequency Permittivity of Biological Tissues with an Open–Ended Coaxial Line: Part 1", IEEE Transactions on Microwave Theory and Techniques, pp. 82–86, vol. MTT–30, No. 1, Jan. 1982.

"Theoretical and Experimental Study of Measurement of Microwave Permittivity using Open Ended Elliptical Coaxial Probes" Y.Xu et al, 0018–9480/92503 1992 IEEE vol. 40, No. 1 Jan. 92, pp. 143–150.

*Primary Examiner*—Michael Brock
*Attorney, Agent, or Firm*—Herbert Dubno

[57] ABSTRACT

A probe (1) is used to measure the dielectric properties of rigid or semi-rigid materials (4), for example, works of art. The probe comprises an inner conductor and an outer, coaxial, conductor separated by a layer of insulator e.g. Teflon (TM). The probe is coupled to a network analyzer (11), which provides microwave frequency radiation which is transmitted by the probe onto the surface of the material where it is reflected back from the surface back down the probe to the analyzer, where it is analyzed to give measurements on the dielectric properties of the material. The probe typically has an outside diameter of around 0.86 mm, and because of its size allows measurements to be made, non-invasively, and in real time on small areas of material. The outside diameter can be made of the order of microns by selecting the frequency of the radiation, which allows measurements to be made in a sample of a semi-rigid material e.g. a layer of paint for depth profiling. The probe has particular application in the measuring of works of art.

5 Claims, 2 Drawing Sheets

5,744,971

DEVICE AND APPARATUS FOR MEASURING DIELECTRIC PROPERTIES OF MATERIALS

FIELD OF THE INVENTION

This invention relates to an apparatus for measuring the dielectric properties of materials suitable, although not exclusively so, for the use in the non-invasive monitoring of the conservation treatment of cultural material e.g. works of art, for example, canvas paintings.

DESCRIPTION OF RELATED ART

The dielectric properties of materials have been extensively used to study the structure, composition and molecular dynamics of materials. This technique is based on the fact that all matter is made of charged particles which respond to an external electric field. Conduction is defined as a finite drift of charges, while polarization is the relative displacement of charges with respect to the applied field. The dielectric properties of a material are interpreted in terms of the electric dipole moment, both permanent (intrinsic) and induced, of the molecules of the material.

As is well known to persons skilled in the art, a polar substance such as a water molecule, has a permanent dipole moment capable of rotating in an applied electromagnetic field. Its relative permittivity, $\epsilon_r$, is not constant as a function of the frequency of the applied electromagnetic field. The complex relative permittivity, can be defined as $$\epsilon^*_r = \epsilon'_r - j\epsilon''_r$$

where $\epsilon'_r$ is the real part of the complex relative permittivity which decreases with increasing frequency of the applied electromagnetic field, $\epsilon''_r$ is the imaginary part of the complex relative permittivity, or the dielectric loss, i.e. it is the absorption of energy by the substance from the applied field which accompanies this fall in permittivity, and j is the square root of −1.

Measurement of permittivity is particularly useful for measuring the presence (or absence) of polar molecules, for example, water (which has a high static permittivity). For example, in the conservation treatment of a painting, in which high relative humidity conditions are used, the ability to measure the moisture content at the surface of the painting and the canvas allows the conservator to be in control of the humidification process.

It is known for dielectric probes to be used to make measurements in solutions and in biological materials, but these are of a dimension not suitable for use on rigid or semi-rigid surfaces, where small areas are to be sampled, for example, small areas of paintings, or where it may be necessary to take measurements within a semi-rigid substance, e.g. within a layer of paint on a painting to carry out depth profiling.

SUMMARY OF THE INVENTION

According to the present invention, there is provided a device for sensing the dielectric properties of a material which comprises an inner conductor, and an outer conductor coaxial with the inner conductor and spaced therefrom by an insulating material. The device has a first open end for contacting with the material and a second end for coupling to means for providing electromagnetic radiation to the inner conductor for transmission thereby to the material through the first open end, and to means for analyzing the electromagnetic radiation transmitted to the material, reflected therefrom and transmitted back to the analyzing means via the outer conductor, the device having an outside diameter of its first open end of less than 1 mm. This has the advantage of allowing in situ non-invasive measurement of the dielectric properties of rigid and semi-rigid materials to be carried out in real time, and because of the dimensions of the probe, it has the spatial resolution to distinguish between adjoining regions of a sample to be monitored, for example between different areas of a painting with differing pigmentation and media. Where the probe has small enough dimensions, i.e. of the order of microns, this enables the probe to be inserted into a semi-rigid materials e.g. layers of paint, to take measurements within to carry out depth profiling.

BRIEF DESCRIPTION OF THE DRAWINGS

The invention will now be described, by way of example only, with reference to the accompanying Figures, of which.

DESCRIPTION OF THE PREFERRED EMBODIMENTS

Figure 1:
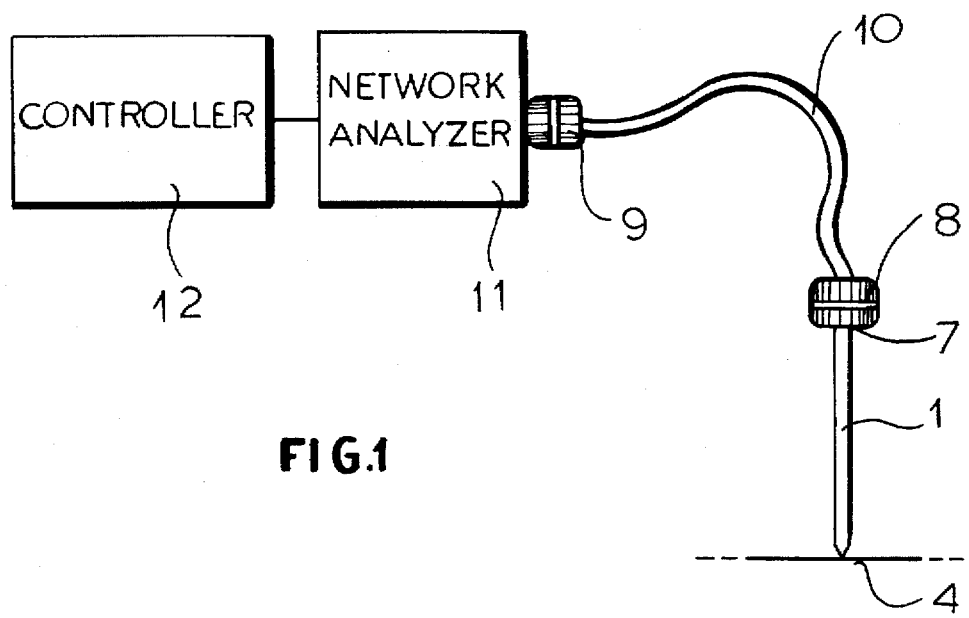
FIG. 1 is a schematic representation of the apparatus for measuring the dielectric properties of materials.
Figure 2:
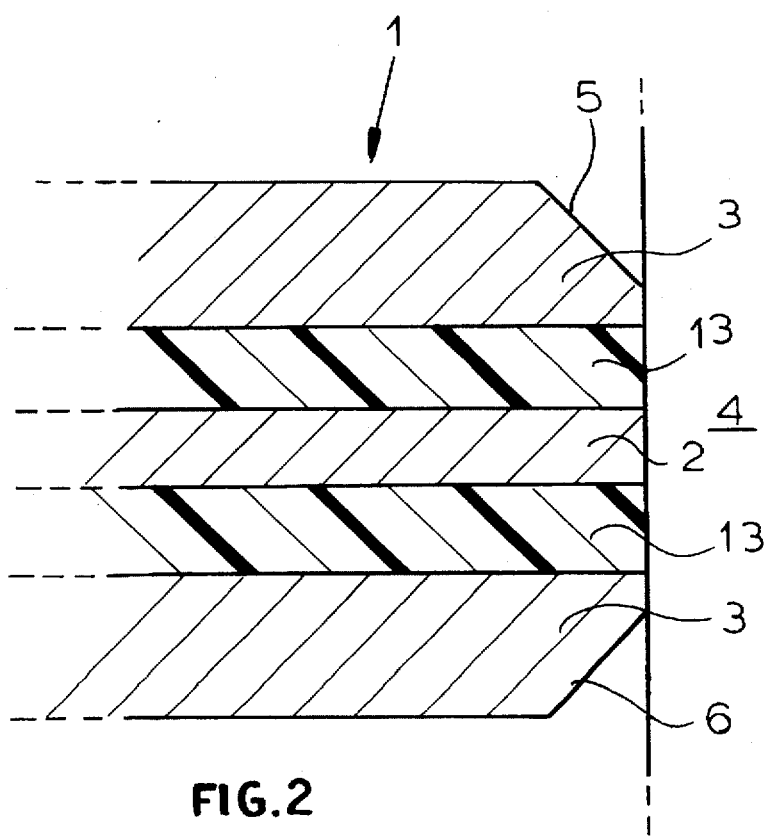
FIG. 2 is a simplified cross-section of the end of a probe for use in the apparatus of FIG. 1 when in contact with a sample to be measured.

A dielectric probe 1 comprises an inner conductor 2, and an outer coaxial conductor 3. The probe 1 is open ended and is configured to contact a sample 4 to be measured at the z=0 plane (in the cylindrical ($\rho,\phi,z$) co-ordinate system), with the z axis at the center of the probe as illustrated in FIG. 2. The outer conductor 3 has bevelled outer edges 5,6 as also illustrated in FIG. 2. Typically, the inner conductor 2 has a diameter a of 0.20 mm, and the outer conductor 3, an inner diameter b of 0.66 mm. The distance between the beginning of the outwardly facing bevelled edges 5,6 is 0.86 mm, i.e. the outside diameter of the probe and, therefore, the diameter of the circular area contacting the surface of the sample of the material to be measured is 0.86 mm. The present invention has particular use in the measurement of rigid and semi-rigid materials. The terms rigid and semi-rigid are particularly herein with reference to cultural materials e.g. paintings and other works of art which typically comprise a canvas backing with layers of paint and glue thereon. However, it will be obvious to persons skilled in the art, that other materials fall within the definition of rigid and semi-rigid materials, e.g. photographic materials.

Insulation 13, e.g. Teflon (TM) is inserted in the region between the outer and inner conductors.

At the other end 7 of the probe 1, the probe 1 is coupled, via known types of connectors e.g. K and SMA connectors 8 and 9, and a known type of flexible 3.5 mm cable 10 to a network analyzer 11 (for example an HP 8220C as manufactured by the Hewlett Packard Corporation). The use and operation of network analyzers is in itself well known to persons skilled in the art, and need not be described in any further detail herein. The network analyzer 11 is controlled by a controller 12.

The network analyzer 11 generates a sweep signal in the range 50 MHz to 20 GHz which is transmitted via the flexible connector 10 to the probe, and, subsequently, down the inner conductor 2, where it impinges on, and penetrates, to some extent, the sample 4 and is then reflected away from the sample 4 back to the outer conductor 3, where the signal is transmitted back up the outer conductor 3, and via the flexible connector 10 to the network analyzer 11. The use of a sweep signal in this frequency range has the advantage that the measurements are fast and can follow the changes taking place in the sample 4 in real time. It is also sensitive to the presence of small polar molecules, e.g. water, which rotate in an applied electromagnetic field at a frequency of 17 GHz at 20° C.

The reflection characteristics at the interface between the sample 4 and the open end of the probe 1 are measured using the network analyzer 11, which then uses these to calculate the dielectric properties of the sample 4, e.g. the relative permittivity and the dielectric loss, for the given frequency of the signal generated by the network analyzer 12. The complex relative permittivity of the sample 4 is related to the reflection coefficient by matching the fields at the boundary of the probe 1 and the sample 4 as $$(Y/2\pi\rho)\int_a^b E_\rho{}^a(\rho)d\rho = (j\_\epsilon/2\pi)\int_a^b \int_0^{2\pi} E_\rho{}^a(\rho) \cos(\Phi'-\Phi) [\exp(-jk_2R_1)]/R_1 d\Phi'd\rho' - \Sigma B_n{}^- \Phi_n{}^-(\rho)$$

The left hand side of this equation represents the difference of the transverse electromagnetic (TEM) wave incident on the sample 4 and the portion which is reflected back along the outer conductor 3. The first term on the right hand side is the magnetic field intensity radiated into the sample 4. The second term on the right hand side represents the higher order modes which are produced at the discontinuity between the probe and the sample and travel back along the outer conductor 3. The primed co-ordinates correspond to simulated source points to predict the magnetic field in the sample region, R is the distance from the source point to a corresponding field point at z=0 and $R^2=\rho^2+\rho'^2-2\rho\rho'\cos(\Phi'-\Phi)$. $E_\rho{}^a(\rho)$ is the electric field at the open end of the probe, Y the admittance, $\Phi_n{}'(\rho)$ is the derivative of the potential function $\Phi_n(\rho)$, with respect to $\rho$ where n is the order of the $TM_{on}$ mode, B is the relative amplitude of the corresponding order mode propagating in the $-z$ direction, $k_2$ is the wave number in the sample 4, and w is the angular frequency. This equation can only be solved numerically.

The apparatus was tested using a number of standards such as air, water, methanol, ethanol, ethanediol and methanamide to provide a simplified model suitable for accurate real time measurement.

The probe can be used in a variety of applications as illustrated by the examples given below:

1. Methanol, used for the non-aqueous de-acidification of canvas, is applied to piece of canvas. The probe can be used to measure how rapidly the methanol evaporates from the canvas;
2. The probe can be used to monitor the dielectric response of a painting undergoing humidity treatment.

Other examples include using the apparatus to monitor moisture uptake in cultural materials, to monitor the cleaning of surfaces of cultural surfaces using both organic and aqueous based preparations, to monitor the effect of exposure of materials to variations in relative humidity, to monitor changes in materials undergoing localised moisture treatment, and to distinguish between the behavior of acrylic, oil, and glue based primed canvases.

Figure 3A:
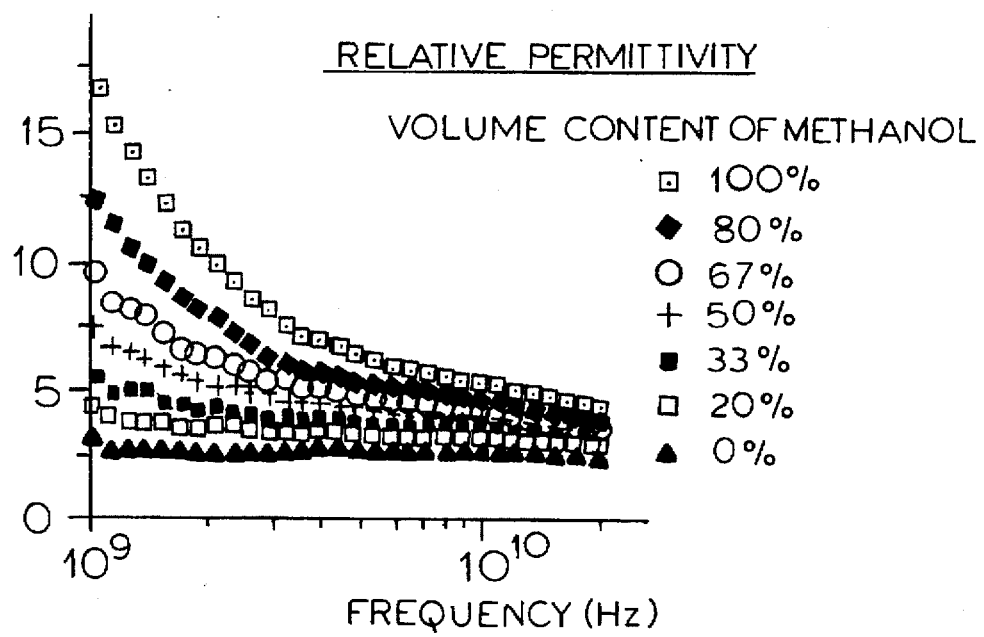
FIGS. 3a and 3b are graphs illustrating relative permittivity and dielectric loss respectively for mixtures of methanol and oil of turpentine.
Figure 3B:
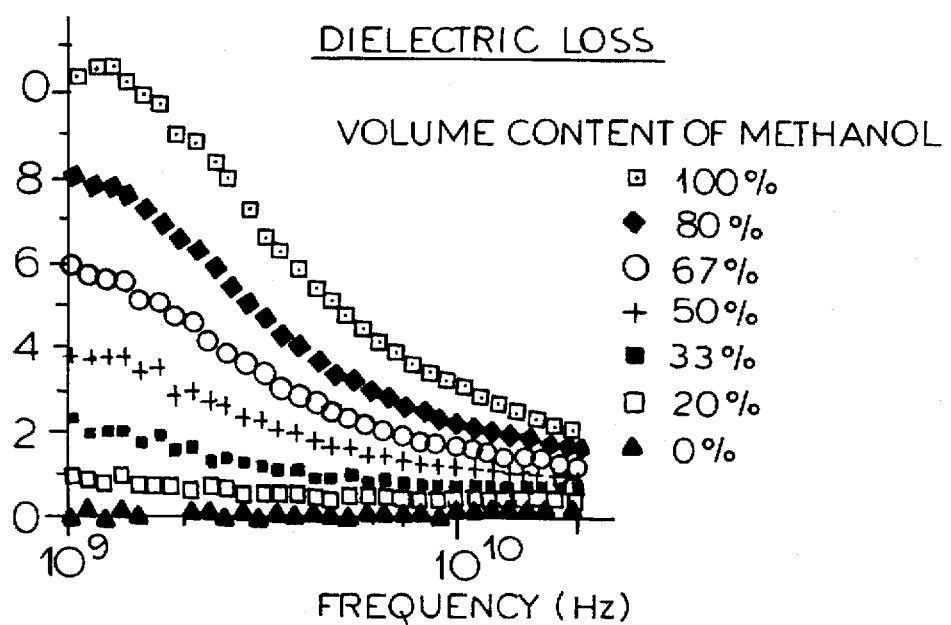

FIGS. 3a and 3b illustrate how the relative permittivity and dielectric loss vary as function of frequency for a variety of mixtures of methanol and oil of turpentine.

It will be obvious to a person skilled in the art, that modifications are possible within the scope of the present invention. For example, frequencies of up to 110 GHz may be possible, and by selecting the appropriate frequency of the radiation, other probe outside diameters are possible, with a range of sizes from a diameter of the order of microns to the order of millimeters (mm) e.g. from 5 microns up to 5 mm. Where the probe has an outside diameter of the order of microns, the probe can actually be inserted into semi-rigid materials e.g. layers of paint, to carry out depth profiling. It can be used to detect the variations in other polar molecules, not only those discussed above. Other suitable insulators can be used between the inner and outer conductors.

What is claimed is:

1. An apparatus for measuring the dielectric properties of rigid and semi-rigid materials, the apparatus comprising a probe having an inner conductor, and an outer conductor coaxial with the inner conductor, the probe having a first open end for contacting with the material without penetrating the surface thereof and a second end coupled to means for providing electromagnetic radiation having a frequency in the microwave range of the electromagnetic spectrum between 50 MHz and 20 GHz to the inner conductor for transmission thereby to the material through the first open end, and to means for analyzing the electromagnetic radiation transmitted to the material, reflected therefrom and transmitted back to the analyzing means via the outer conductor to provide a measurement of the dielectric properties of the material therefrom and to determine the moisture content of the material from the following formula:

$$(Y/2\pi\rho)\int_a^b E_\rho{}^a(\rho)d\rho = (j\_\epsilon/2\pi)\int_a^b \int_0^{2\pi} E_\rho{}^a(\rho) \cos(\Phi'-\Phi) [\exp(-jk_2R_1)]/R_1 d\Phi'd\rho' - \Sigma B_n{}^- \Phi_n{}^-(\rho),$$

wherein the primed coordinates correspond to simulated source points to predict the magnetic field in the sample region, R is the distance from the source point to a corresponding field point at z=0 and $R^2=\rho^2+\rho'^2-2\rho\rho'\cos(\Phi'-\Phi)$, $E_{\rho a}(\rho)$ is the electric field at the open end of the probe, Y the admittance, $\Phi_n{}'(\rho)$ is the derivative of the potential function $\Phi_n(\rho)$, with respect to $\rho$ where n is the order of the $Tm_{on}$ mode, B is the relative amplitude of the corresponding order mode propagating in the $-z$ direction, $k_2$ is the wave number in the sample, and w is the angular frequency.

2. An apparatus according to claim 1 wherein the outer conductor has an outside diameter of less than one millimeters.

3. An apparatus according to claim 1 wherein the probe has a tip engageable with cultural material.

4. A device for sensing the dielectric properties of a material, comprising an inner conductor, and an outer conductor coaxial with the inner conductor, the device having a first open end for contacting with the material and a second end for coupling to means for providing electromagnetic radiation said radiation having a frequency in the microwave range of the electromagnetic spectrum of 50 MHz to 20 GHz, to the inner conductor for transmission thereby to the material through the first open end, and to means for analyzing the electromagnetic radiation transmitted to the material, reflected therefrom and transmitted back to the analyzing means via the outer conductor, the outer conductor at the first open end being bevelled on its outer perimeter, and said outer conductor having an outside diameter at the first open end of less than 1 mm.

5. A device according to claim 4, wherein the outer conductor and inner conductor are separated by an insulating material.

* * * * *